United States Patent [19]

Shiraki et al.

[11] Patent Number: 4,886,933

[45] Date of Patent: Dec. 12, 1989

[54] PRODUCTION OF LINEAR ALPHA-OLEFINS

[75] Inventors: Yasushi Shiraki; Takao Tamura, both of Tokuyama, Japan

[73] Assignee: Idemitsu Petrochemical Co., Ltd., Tokyo, Japan

[21] Appl. No.: 221,724

[22] Filed: Jul. 20, 1988

[30] Foreign Application Priority Data

Feb. 15, 1988 [JP] Japan .................................. 63-30840

[51] Int. Cl.$^4$ ................................. C07C 2/02
[52] U.S. Cl. .................................. 585/522; 585/523; 502/112; 502/117
[58] Field of Search .............................. 585/522, 523

[56] References Cited

U.S. PATENT DOCUMENTS 4,486,615 12/1984 Langer, Jr. ........................... 585/523
4,783,573 11/1988 Shiraki et al. ....................... 585/523

FOREIGN PATENT DOCUMENTS 0241596 10/1987 European Pat. Off. .
58-109428  6/1983 Japan .
58-113138  7/1983 Japan .
58-201729 11/1983 Japan .
62-243605 10/1987 Japan .
63-41430   2/1988 Japan .

OTHER PUBLICATIONS

Patent Abstracts of Japan, unexamined applications, field C, vol. 11, No. 167, May 28, 1987.
Patent Abstracts of Japan, unexamined applications, field C, vol. 11, No. 259, Aug. 21, 1981.

Primary Examiner—Patrick P. Garvin
Attorney, Agent, or Firm—Frishauf, Holtz, Goodman & Woodward

[57] ABSTRACT

In a method for the production of linear α-olefins by the oligomerization of ethylene in the presence of a catalyst system composed of (A) zirconium tetrachloride, (B-a) ethyl aluminum sesquichloride and (B-b) triethyl aluminum, an improvement is proposed which comprises using the catalyst system prepared in a specific procedure in which one of the essential conditions is the order of successive introduction of the three components along with the concentration of zirconium tetrachloride, temperature and length of time. It is essential that introduction of the component (B-b) is not preceded by the contacting of the components (A) and (B-a). Accoridng to the invention, the reaction product contains the species of the linear α-olefin compounds having higher usefulness than other species in a greatly increased yield.

11 Claims, No Drawings

PRODUCTION OF LINEAR ALPHA-OLEFINS

BACKGROUND OF THE INVENTION

The present invention relates to an improvement in the production of linear α-olefins. More particularly, the present invention relates to an improvement in the method for the production of linear α-olefins useful as a comonomer for modifying polyolefins or as a starting material for the manufacture of plasticizers, surface active agents and the like by using a catalyst having a high activity and excellent stability, in which the product can be obtained in a high purity and with an optimum distribution of the respective α-olefin compounds relative to the increased yields of the most useful α-olefin compounds having 6 to 18 carbon atoms in a molecule.

As is well known, linear α-olefins are useful, for example, as a comonomer for the modification of polyolefins or as a starting material for the manufacture of plasticizers, surface active agents and the like. In this regard, linear α-olefin compounds having 6 to 18 carbon atoms are particularly useful and widely used in large quantities.

These linear α-olefin compounds are prepared usually by the catalytic oligomerization of ethylene in the presence of a so-called Ziegler-type catalyst. Various types of catalysts are known to be suitable for the purpose including, for example, a binary catalyst system comprising an ethyl aluminum chloride as combined with titanium tetrachloride as the transition metal compound, optionally, with further admixture of a third ingredient with an object to enhance the selectivity.

The above mentioned catalyst systems using a titanium compound are not quite satisfactory in respect of the activity and selectivity of the catalyst.

On the other hand, several catalyst systems for the production of linear α-olefins have been proposed in which a zirconium compound is used as the transition metal compound (see, for example, Japanese patent Kokai 58-109428, 58-113138 and 58-201729).

Although the catalytic activity of these catalyst systems using a zirconium compound is higher than that of the above mentioned catalyst systems using a titanium compound, they have some problems and disadvantages that waxy materials as a by-product are produced in a very large amount (see Japanese patent Kokai 58-109428 and 58-113138) and that the oligomers having 4 carbon atoms in a molecule are produced in an extremely high yield and the purity of the linear α-olefin product is relatively low (see Japanese patent Kokai 58-201729).

SUMMARY OF THE INVENTION

The present invention accordingly has an object to improve the performance of the catalyst conventionally used in the production of linear α-olefins and to provide an improved method for the production of linear α-olefins in a high purity having an optimum distribution of the respective compounds relative to the increased yields of the linear α-olefin compounds having 6 to 18 carbon atoms in a molecule, which are the most useful compounds among the linear α-olefin compounds, by using a catalyst system having high catalytic activity and excellent stability.

Thus, the present invention completed as a result of the investigations extensively undertaken with the above mentioned object provides an improvement which comprises, in a method for the production of linear α-olefin compounds by the oligomerization of ethylene in the presence of a catalyst which is a mixture composed of:

(A) a zirconium halide represented by the general formula

$$ZrX_aA_{4-a}$$

in which X and A, which may be the same or different from each other, are each an atom of a halogen selected from the group consisting of chlorine, bromine and iodine and the subscript a is zero or a positive integer not exceeding 4;

(B-a) a first alkyl aluminum compound represented by the general formula $$AlR_{1.5}Q_{1.5}$$

in which R is an alkyl group having 1 to 20 carbon atoms and Q is an atom of a halogen selected from the group consisting of chlorine, bromine and iodine, R and Q each optionally being a combination of two kinds or more of the alkyl groups and halogen atoms, respectively; and (B-b) a second alkyl aluminum compound represented by the general formula

$$AlR'_bQ'_{3-b}$$

in which R' is an alkyl group having 1 to 20 carbon atoms, Q' is an atom of a halogen selected from the group consisting of chlorine, bromine and iodine, R' and Q' each optionally being a combination of two kinds or more of the alkyl groups and halogen atoms, respectively, and b is 1, 2 or 3, and a ligand composed of at least one kind of the compounds selected from the group consisting of sulfur compounds, phosphorus compounds and nitrogen compounds, using a catalyst composed of the components (A), (B-a) and (B-b) and prepared by a process in which:

(1) the concentration of the zirconium halide as the component (A) is in the range from 40 to 140 m moles per liter of a solvent;

(2) the temperature for the preparation of the catalyst is in the range from 40° to 75° C. when the solvent is an aromatic hydrocarbon compound or in the range from 50° to 100° C. when the solvent is an alicyclic hydrocarbon compound;

(3) the length of time for the preparation of the catalyst is in the range from 10 minutes to 8 hours; and (4) the catalyst is prepared by successively introducing the components in an order of, first, the zirconium halide as the component (A), second, the second alkyl aluminum compound as the component (B-b) and, third, the first alkyl aluminum compound as the component (B-a).

The above mentioned introducing order of the catalyst components can be modified in several different ways. For example, the first alkyl aluminum compound as the component (B-a) and the second alkyl aluminum compound as the component (B-b) can be introduced simultaneously following introduction of the zirconium halide as the component (A). Alternatively, the zirconium halide as the component (A) can be introduced after introduction of the first alkyl aluminum compound as the component (B-a) and the second alkyl aluminum compound as the component (B-b). Further, the three components can be introduced successively in an order of, first, the second alkyl aluminum compound as the component (B-b), second, the zirconium halide as the component (A) and, third, the first alkyl aluminum compound as the component (B-a). Alternatively, said components can be introduced successively in an order of, first, the second alkyl aluminum compound as the component (B-b), second, the first alkyl aluminum compound as the component (B-a) and, third, the zirconium halide as the component (A).

DETAILED DESCRIPTION OF THE PREFERRED EMBODIMENTS

The above described improvement of the present invention has been established on the base of an unexpected discovery that the problems and disadvantages in the prior art methods for the production of linear α-olefin compounds can be dissolved when the oligomerization reaction of ethylene is performed in the presence of a catalyst system, which is formed from a specific zirconium halide and two kinds of specific alkyl aluminum compounds used in a specific sequential order of introduction at a specified temperature taking a specified length of time, as combined with a specific ligand.

The catalyst system used in the production of linear α-olefins is composed of a zirconium halide as the component (A) and two kinds of alkyl aluminum compounds as the components (B-a) and (B-b).

The zirconium halide as the component (A) is represented by the general formula $$ZrX_aA_{4-a} \qquad (I)$$

in which X, A and a each have the meaning as defiend above. X and A in the compound can be the same ones or different ones from each other. Examples of suitable zirconium halide compounds include $ZrCl_4$, $ZrBr_4$, $ZrI_4$, $ZrBrCl_3$, $ZrBr_2Cl_2$ and the like, of which $ZrCl_4$ is preferred. These zirconium halide compounds can be used either singly or as a combination of two kinds or more according to need.

The first alkyl aluminum compound as the component (B-a) of the catalyst system is represented by the general formula $$AlR_{1.5}Q_{1.5} \qquad (II)$$

in which R and Q each have the meaning as defined above. The alkyl group denoted by R has 1 to 20 carbon atoms. The above given general formula (II) is equivalent to the formula $Al_2R_3Q_3$. Examples of suitable alkyl aluminum compounds as the component (B-a) include $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3I_3$, $Al_2(C_2H_5)_3BrCl_2$, $Al_2(C_3H_7)_3Cl_3$, $Al_2(iso-C_3H_7)_3Cl_3$, $Al_2(C_4H_9)_3Cl_3$, $Al_2(iso-C_4H_9)_3Cl_3$, $Al_2(C_5H_{11})_3Cl_3$, $Al_2(C_8H_{17})_3Cl_3$, $Al_2(C_2H_5)_2(CH_3)Cl_3$ and the like. Preferable ones among them are those having methyl, ethyl, propyl and butyl groups or, more preferably, those having ethyl groups. The halogen atom denoted by Q is preferably a chlorine atom. An example of such a preferable alkyl aluminum compound is ethyl aluminum sesquichloride of the formula $Al_2(C_2H_5)_3Cl_3$. These alkyl aluminum compounds can be used either singly or as a combination of two kinds or more according to need as the component (B-a).

The second alkyl aluminum compound as the component (B-b) is represented by the general formula $$AlR'_bQ'_{3-b} \qquad (III)$$

in which R', Q' and b each have the meaning defined above. The alkyl group denoted by R' has 1 to 20 carbon atoms. Examples of alkyl aluminum compounds suitable as the component (B-b) include $Al(CH_3)_3$, $Al(C_2H_5)_3$, $Al(C_3H_7)_3$, $Al(iso-C_3H_7)_3$, $Al(C_4H_9)_3$, $Al(iso-C_4H_9)_3$, $Al(C_5H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)Br_2$, $Al(C_2H_5)I_2$ and the like. Preferable ones among them are those having ethyl, propyl and butyl groups as the alkyl group denoted by R' or, more preferably, those having ethyl groups. The halogen atom denoted by Q' is preferably a chlorine atom. The subscript b is preferably 2 or 3. Examples of the alkyl aluminum compounds preferable as the component (B-b) are triethyl aluminum and diethyl aluminum chloride. These alkyl aluminum compounds as the component (B-b) can be used either singly or as a combination of two kinds or more according to need.

The catalyst system used in the production of linear α-olefins is prepared in an inert organic solvent. Examples of suitable organic solvents include aromatic hydrocarbon solvents unsubstituted or substituted with halogens such as benzene, toluene, xylene, chlorobenzene, ethyl benzene, dichlorobenzene, chlorotoluene and the like, aliphatic paraffin hydrocarbons such as pentane, hexane, heptane, octane, nonane, decane and the like, alicyclic hydrocarbon compounds such as cyclohexane, decahydronaphthalene and the like, halogenated alkanes such as dichloroethane, dichlorobutane and the like, and so on.

The catalyst system is prepared at a temperature in the range from 40° to 75° C. or, preferably, from 50° to 70° C. when an aromatic hydrocarbon compound is used as the solvent and in the range from 50° to 100° C. or, preferably, from 60° to 80° C. when an alicyclic hydrocarbon compound is used as the solvent. When the temperature is lower than the above mentioned lower limit, the product of linear α-olefin compounds obtained thereby may have a somewhat decreased purity. When the temperature is too high, on the other hand, the production of heavier materials having 20 or more of carbon atoms in a molecule, such as waxes, may be increased as a trend. The catalyst system is prepared taking a length of time in the range from 10 minutes to 8 hours or, preferably, from 30 minutes to 3 hours.

The concentration of the zirconium halide as the component (A) in the preparation of the catalyst system is selected in the range from 40 to 140 m moles per liter of the solvent or, preferably, from 60 to 120 m moles per liter of the solvent in respect of the desirable distribution of the respective useful species of the linear α-olefin compounds as well as in respect of the activity and stability of the catalyst system. When the concentration is too low, the activity of the catalyst system may be subject to gradual decrease in the lapse of time resulting in an increase in the production of lighter fractions. When the concentration is too high, on the other hand, the activity of the catalyst system also decreases gradually in the lapse of time and the resultant product may contain the heavier fractions in an extremely increased proportion.

According to the results of the investigations, the performance of the catalyst system is greatly influenced by the order of the successive introduction of the above described three components at the time of preparing the catalyst. It was found that satisfactory results could be obtained only when the components were introduced in either one of the following four orders. Firstly, the zirconium halide as the comonent (A) is first introduced in the solvent followed by the successive introduction of the second alkyl aluminum compound as the component (B-b) and then the first alkyl aluminum compound as the component (B-a) in this order. Secondly, the zirconium halide as the component (A) is first introduced followed by the simultaneous introduction of the first and the second alkyl aluminum compounds as the components (B-a) and (B-a). Thirdly, the introduction of the zirconium halide as the component (A) follows the introduction of the first and the second alkyl aluminum compounds as the components (B-a) and (B-b). In this case, the order of the introduction of the components (B-a) and (B-b) is not limitative and either one of them can be first introduced followed by the introduction of the other. Of course, the components (B-a) and (B-b) can be introduced simultaneously. Fourthly, the second alkyl aluminum compound as the component (B-b) is first introduced followed by the successive introduction of the zirconium halide compound as the component (A) and then the first alkyl aluminum compound as the component (B-a) in this order. At any rate, the activity of the catalyst system is greatly decreased when the catalyst system is prepared by introducing the three components in a different order from the above mentioned four orders.

As a possibility, water, though in a very small amount, may be present in the catalyst preparation system of an actual production line. When the zirconium halide is first introduced into such a water-containing system, the active sites for the reaction are deactivated by the reaction with the water along with formation of the hydrogen halide.

It is therefore preferable to first introduce the alkyl aluminum compound as the component (B) in order to avoid such troubles. As is mentioned above, the respective ingredients of the catalyst system can be introduced in four different sequential orders, of which the third and the fourth are preferred. In these procedures, namely, the component (B) is first introduced and, more preferably, the component (B-b) should be first introduced.

Following is an explanation of a presumable reason for the significance of the order in which the three catalyst components are introduced as mentioned above. Namely, the active points for the reaction are on the zirconium halide compound, e.g., $ZrCl_4$, as the transition metal ingredient while the catalytic activity can be exhibited only after formation of a complex thereof with the alkyl aluminum compound. The catalytic activity is higher when an increased amount of the second alkyl aluminum compound as the component (B-b) relative to the first alkyl aluminum compound is coordinated with the transition metal ingredient.

Further, the second alkyl aluminum compound as the component (B-b) has a higher activity for the coordination to a transition metal than the first alkyl aluminum compound as the component (B-a) and no decrease is caused in the catalytic activity of the catalyst system when a zirconium halide compound is added to a mixture of the first and the second alkyl aluminum compounds or the mixture of the alkyl aluminum compounds is added to the zirconium halide compound. On the contrary, no catalyst system having sufficinetly high activity can be obtained when the first alkyl aluminum compound as the component (B-a) alone is first brought into contact with the zirconium halide as a transition metal compound presumably due to the disturbed coordination of the second alkyl aluminum compound as the component (B-b) subsequently introduced to the complex of the transition metal compound and the first alkyl aluminum compound. This is the reason for the significance of the above mentioned four orders of the introduction of the three catalyst components at the time of preparing the catalyst.

As to the proportion of the three components used for forming the catalyst system, it is usual that the component (A) and the components (B-a) and (B-b) are combined in such a proportion that the molar ratio of aluminum to zirconium Al:Zr is in the range from 1 to 15. The component (B-a) and the component (B-b) are combined usually in such a proportion that the molar ratio of (B-a):(B-b) is in the range from 2 to 10.

In the method for the production of linear $\alpha$-olefin compounds according to the improvement of the invention, the catalyst system prepared in the above described manner is used for the oligomerization reaction of ethylene in combination with at least one kind of the compounds selected from the group consisting of sulfur compounds, phosphorus compounds and nitrogen compounds as the ligand.

Though not particularly limitative, examples of suitable sulfur compounds include, for example, thioether compounds such as dimethyl sulfide, diethyl sulfide, dipropyl sulfide, dihexyl sulfide, dicyclohexyl sulfide, diphenyl thioether and the like; dialkyl disulfide compounds such as dimethyl disulfide, diethyl disulfide, dipropyl disulfide, dibutyl disulfide, dihexyl disulfide, ethyl methyl disulfide and the like; thiophene compounds such as thiophene, 2-methyl thiophene, 3-methyl thiophene, 2,3-dimethyl thiophene, 2-ethyl thiophene, benzothiophene and the like; heterocyclic sulfur compounds such as tetrahydrothiophene, thiopyrane and the like; aromatic sulfur compounds such as diphenyl sulfide, diphenyl disulfide, methyl phenyl disulfide, methyl phenyl sulfide and the like; sulfide compounds such as thiourea, methyl sulfide, ethyl sulfide, butyl sulfide and the like; and so on.

Though not particularly limitative, examples of suitable phosphorus compounds include, for example, phosphine compounds such as triphenyl phosphine, triethyl phosphine, tributyl phosphine, tripropyl phosphine, trioctyl phosphine, tricyclohexyl phosphine and the like.

Though not particularly limitative, examples of suitable nitrogen compounds include, for example, organic amine compounds such as methyl amine, ethyl amine, propyl amine, butyl amine, pentyl amine, hexyl amine, cyclohexyl amine, octyl amine, decyl amine, aniline, benzyl amine, naphthyl amine, dimethyl amine, diethyl amine, dibutyl amine, diphenyl amine, triethyl amine, tributyl amine, triphenyl amine, pyridine, picoline and the like.

Among the above named sulfur compounds, phosphorus compounds and nitrogen compounds, particularly preferable compounds as the ligand include dimethyl disulfide, thiophene, thiourea, triphenyl phosphine, tributyl phosphine, trioctyl phosphine and aniline. These compounds as the ligand can be used either singly or as a combination of two kinds or more according to need.

The amount of the above named ligand compound used in combination with the catalyst system is, per mole of the zirconium halide compound as the component (A) of the catalyst system, usually in the range from 1 to 20 moles when the ligand compound is a sulfur compound and in the range from 0.5 to 10 moles when the ligand compound is a phosphorus compound or nitrogen compound.

The oligomerization reaction of ethylene according to the improvement of the present invention is carried out by using the above described catalyst system in the presence of the ligand compound. It is usual that the reaction is performed by using an organic solvent as the reaction medium. Examples of the organic solvents suitable as the reaction medium may be the same ones as those given as the examples of the organic solvent used in the preparation of the catalyst system. The oligomerization reaction of ethylene is carried out usually at a temperature in the range from 100° to 150° C. under a pressure of at least 25 kg/cm$^2$G. Although the length of time for the reaction is variable depending on the temperature and pressure, the reaction is usually complete within 15 minutes to about 1 hour.

After completion of the oligomerization reaction, the unreacted ethylene dissolved in the reaction mixture is vaporized and removed therefrom by the method of adiabatic flashing and then the reaction mixture is subjected to a deactivation treatment of the catalyst and deashing treatment followed by distillation to separate and isolate the solvent and the linear α-olefin compounds as the product. The unreacted ethylene and the solvent as recovered are recycled to and re-used in the subsequent runs of the reaction. The product is a mixture of various α-olefin compounds having 4 or more of carbon atoms in a molecule produced by the polymerization reaction of ethylene. Multistage distillation can be used successfully for the isolation of the respective α-olefin compounds from the mixture as the product. It is an advantageous way that the yield of a desired α-olefin compound having a particular number of carbon atoms in a molecule is increased relative to other α-olefin compounds by appropriately selecting and controlling the reaction conditions.

When the improvement of the invention is applied to the preparation of the catalyst system by introducing the components (A), (B-a) and (B-b) in a specific order of successive introduction and by performing the preparation thereof under specific conditions, the catalyst system thus prepared is imparted with greatly increased activity and stability and the reaction product obtained by using the catalyst contains the respective linear α-olefin compounds in an optimum distribution of the compounds in favor of the compounds having high utilizability.

In the following, examples are given to illustrate the improvement of the invention in more detail but not to limit the scope of the invention in any sense.

EXAMPLE 1

[1] Preparation of catalyst solution

Into a flask of 1000 ml capacity equipped with a stirrer were introduced 50 m moles of anhydrous zirconium tetrachloride and 500 ml of dry benzene under an atmosphere of argon and the mixture was agitated for 10 minutes followed by addition of 41.7 m moles of triethyl aluminum $(C_2H_5)_3Al$ and further continued agitation for about 10 minutes. Thereafter, 208.3 m moles of ethyl aluminum sesquichloride $(C_2H_5)_3Al_2Cl_3$ were added to the mixture and the mixture was further agitated at 60° C. for 30 minutes to form a complex. The molar ratios of Al:Zr and $(C_2H_5)_3Al_2Cl_3:(C_2H_5)_3Al$ were each 5.

Into a three-necked flask of 500 ml capacity, thereafter, were introduced 250 ml of benzene and the above obtained complex solution in an amount to give 0.05 m mole of $ZrCl_4$, 0.21 m mole of $(C_2H_5)_3Al_2Cl_3$ and 0.04 m mole of $(C_2H_5)_3Al$ and the mixture was agitated for 10 minutes at room temperature to give a catalyst solution.

[2] Production of linear α-olefins

The catalyst solution prepared in [1] above was introduced into an autoclave of 1 liter capacity equipped with a stirrer under an atmosphere of dry argon by feeding with pressurized argon gas. Thereafter, 0.30 m mole of thiophene was added to the autoclave. The temperature of the autoclave was kept at 50° to 60° C. throughout. When addition of the catalyst solution and thiophene had been completed, agitation of the mixture was started and high-purity ethylene gas was introduced into the autoclave under pressurization until the pressure inside the autoclave had reached 65 kg/cm$^2$G followed by elevation of the temperature up to 120° C. Introduction of ethylene was continued at such a rate that the above mentioned pressure could be maintained and the reaction was effected for 30 minutes under the conditions of temperature and pressure maintained. Thereafter, an aqueous solution of sodium hydroxide was introduced into the autoclave under pressurization to terminate the reaction by the deactivation of the catalyst. The reaction mixture after completion of the reaction was cooled and subjected to a post-treatment in the following manner.

In the first place, the reaction mixture was admixed with 20 g of undecane to serve as an internal standard in the gas chromatographic analysis and then filtered by using a filter paper to remove the waxy material. The waxy material on the filter paper was thoroughly washed with benzene to remove the lighter fraction in the wax and the washings were combined with the filtrate of the reaction mixture. The filtrate of the reaction mixture was twice washed each time with 500 ml of pure water and then dehydrated over anhydrous potassium carbonate.

The clear reaction product obtained in the above described manner was subjected to gas chromatographic analysis to determine the yield of the product by the internal standard method. On the other hand, the waxy material separated by filtration was air-dried and further dried in a vacuum desicator under a pressure of 20 mmHg to determine the weight. The yeild of the $C_4$ to $C_6$ fractions was calculated from the Schultz-Flory distribution in order to avoid a possible error in the actual yield due to the loss caused in handling of the material. The results are shown in Table 1 below.

EXAMPLE 2

The experimental procedure was substantially the same as in Example 1 except that the length of time taken for the preparation of the catalyst was 120 minutes instead of 30 minutes. The results are shown in Table 1.

EXAMPLE 3

The experimental procedure was substantially the same as in Example 1 except that the amounts of zirconium tetrachloride, ethyl aluminum sesquichloride and triethyl aluminum were each increased to 0.1 m mole, 0.58 m mole and 0.12 m mole, respectively, and the amount of thiophene as the ligand was 0.60 m mole instead of 0.30 m mole, and the molar ratio of Al/Zr was 7 instead of 5. The results are shown in Table 1.

EXAMPLE 4

The experimental procedure was substantially the same as in Example 3 except that the length of time taken for the preparation of the catalyst was 120 minutes instead of 30 minutes. The results are shown in Table 1.

EXAMPLE 5

The experimental procedure was substantially the same as in Example 1 except that the complex solution was prepared at 70° C. instead of 60° C. taking 120 minutes instead of 30 minutes. The results are shown in Table 1.

COMPARATIVE EXAMPLE 1

The experimental procedure was substantially the same as in Example 1 except that the complex solution was prepared at 20° C. instead of 60° C. The results are shown in Table 1.

COMPARATIVE EXAMPLE 2

The experimental procedure was substantially the same as in Example 1 except that the complex solution was prepared at 80° C. instead of 60° C. The results are shown in Table 1.

COMPARATIVE EXAMPLE 4

The experimental procedure was substantially the same as in Example 1 except that, in the preparation of the complex solution, the introduction of zirconium tetrachloride was followed by the successive introduction of ethyl aluminum sesquichloride and then triethyl aluminum. The results are shown in Table 1.

EXAMPLE 7

The experimental procedure was substantially the same as in Example 6 except that, in the preparation of the complex solution, zirconium tetrachloride was introduced following the simultaneous introduction of ethyl aluminum sesquichloride and triethyl aluminum instead of first introducing zirconium tetrachloride. The results are shown in Table 1.

EXAMPLE 8

The experimental procedure was substantially the same as in Example 2 except that the complex solution was prepared at 50° C. instead of 60° C. The results are shown in Table 1.

EXAMPLE 9

The experimental procedure was substantially the same as in Example 8 except that the length of time taken for the preparation of the complex solution was 240 minutes instead of 120 minutes. The results are shown in Table 1.

TABLE 1

| | Catalytic activity, g α-olefin g ZrCl$_4$ | Composition of linear α-olefin product, % by weight | | | | | Purity of C$_{18}$ fraction, % by weight |
|---|---|---|---|---|---|---|---|
| | | C$_4$ fraction | C$_6$ fraction | C$_8$ fraction | C$_{10}$ to C$_{18}$ fraction | C$_{20}$+ fraction | |
| Example 1 | 9320 | 15.1 | 15.6 | 15.2 | 41.5 | 12.6 | 95.2 |
| Example 2 | 11550 | 14.8 | 15.2 | 13.7 | 40.2 | 16.1 | 96.7 |
| Example 3 | 8590 | 17.5 | 17.2 | 15.1 | 38.2 | 12.0 | 95.0 |
| Example 4 | 8360 | 17.5 | 17.2 | 15.6 | 38.7 | 11.0 | 93.7 |
| Example 5 | 9660 | 14.6 | 15.0 | 13.2 | 40.7 | 16.5 | 97.0 |
| Comparative Example 1 | 3800 | 16.0 | 16.4 | 14.6 | 40.6 | 12.4 | 95.2 |
| Example 2 | 17500 | 11.1 | 12.1 | 11.9 | 39.7 | 25.2 | 89.2 |
| Example 3 | 4010 | 19.6 | 18.6 | 16.0 | 37.3 | 8.5 | 92.1 |
| Example 6 | 7810 | 15.9 | 16.3 | 19.5 | 40.0 | 8.3 | 95.1 |
| Comparative Example 4 | 2300 | 18.0 | 17.5 | 15.3 | 39.0 | 10.2 | 96.0 |
| Example 7 | 9690 | 15.2 | 15.4 | 14.0 | 40.2 | 15.2 | 95.0 |
| Example 8 | 9700 | 14.8 | 15.2 | 13.8 | 40.2 | 16.0 | 97.4 |
| Example 9 | 8900 | 14.9 | 15.1 | 14.0 | 40.1 | 15.9 | 97.0 |

COMPARATIVE EXAMPLE 3

The experimental procedure was substantially the same as in Example 3 except that the complex solution was prepared at 25° C. instead of 60° C. The results are shown in Table 1.

EXAMPLE 6

The experimental procedure was substantially the same as in Example 1 except that, in the preparation of the complex solution, the introduction of zirconium tetrachloride was followed by the simultaneous introduction of triethyl aluminum and ethyl aluminum sesquichloride instead of the successive introduction of triethyl aluminum and then ethyl aluminum sesquichloride. The results are shown in Table 1.

EXAMPLE 10

The experimental procedure was substantially the same as in Example 1 except that the concentration of zirconium tetrachloride in the preparation of the complex solution was decreased to 70 m moles per liter of the solvent from 100 m moles per liter and the catalyst as prepared was cooled to room temperature and used after storage for 1, 5 and 10 days. The results are shown in Table 2 below.

EXAMPLE 11

The experimental procedure was just the same as in Example 1 except that the catalyst as prepared was cooled to room temperature and used after storage for 1, 5 and 10 days. The results are shown in Table 2.

COMPARATIVE EXAMPLE 5

The experimental procedure was substantially the same as in Example 1 except that the concentration of zirconium tetrachloride in the preparation of the complex solution was decreased from 100 m moles per liter of the solvent to 30 m moles per liter and the catalyst as prepared was cooled to room temperature and used after storage for 1, 5 and 10 days. The results are shown in Table 2.

COMPARATIVE EXAMPLE 6

The experimental procedure was substantially the same as in Example 1 except that the concentration of zirconium tetrachloride in the preparation of the complex solution was increased from 100 m moles per liter of the solvent to 150 m moles per liter and the catalyst as prepared was cooled to room temperature and used after storage for 1, 5 and 10 days. The results are shown in Table 2.

TABLE 2

|  | Days of catalyst storage | Catalytic activity, g α-olefin/ g ZrCl$_4$ | Composition of linear α-olefin product, % by weight | | | | | Purity of C$_{18}$ fraction, % by weight |
|---|---|---|---|---|---|---|---|---|
|  |  |  | C$_4$ fraction | C$_6$ fraction | C$_8$ fraction | C$_{10}$ to C$_{18}$ fraction | C$_{20}$+ fraction |  |
| Example 10 | 1 | 8150 | 14.7 | 15.2 | 13.2 | 41.7 | 15.2 | 95.3 |
|  | 5 | 9440 | 15.6 | 15.8 | 14.3 | 42.3 | 12.0 | 94.8 |
|  | 10 | 8580 | 15.5 | 16.0 | 14.3 | 43.0 | 11.2 | 95.1 |
| Example 11 | 1 | 9320 | 15.1 | 15.6 | 15.2 | 41.5 | 12.6 | 95.2 |
|  | 5 | 8930 | 14.9 | 15.4 | 14.5 | 42.5 | 12.7 | 95.4 |
|  | 10 | 9410 | 15.0 | 15.5 | 14.9 | 42.2 | 12.4 | 95.1 |
| Comparative Example 5 | 1 | 11930 | 5.1 | 6.3 | 6.7 | 32.1 | 49.8 | 96.8 |
|  | 5 | 8600 | 14.2 | 14.9 | 13.3 | 42.2 | 15.4 | 95.2 |
|  | 10 | 7810 | 15.0 | 15.4 | 13.9 | 40.3 | 15.4 | 94.5 |
| Comparative Example 6 | 1 | 6870 | 5.3 | 6.6 | 7.6 | 37.7 | 42.8 | 96.2 |
|  | 5 | 6950 | 6.4 | 7.7 | 8.0 | 37.0 | 40.9 | 96.1 |
|  | 10 | 4300 | 7.8 | 9.3 | 9.0 | 43.5 | 30.4 | 95.8 |

EXAMPLE 12

The experimental procedure was about the same as in Example 1 except that the solvent was cyclohexane instead of benzene, the amounts of zirconium tetrachloride, ethyl aluminum sesquichloride and triethyl aluminum were 0.05 m mole, 0.272 m mole and 0.078 m mole, respectively, to give the molar ratios of Al:Zr of 7 and (C$_2$H$_5$)$_3$Al$_2$Cl$_3$:(C$_2$H$_5$)$_3$Al of 3.5 and the concentration of zirconium tetrachloride of 100 m moles per liter of the solvent, the complex solution was prepared at 70° C. taking 180 minutes and the catalyst as prepared was cooled to room temperature and used after storage of 1, 5 and 10 days. The results are shown in Table 3 below.

EXAMPLE 13

The experimental procedure was substantially the same as in Example 12 except that the complex solution was prepared at 60° C. taking 30 minutes. The results are shown in Table 3.

When cyclohexane was used as the solvent and the complex solution was prepared at a relatively low temperature, it was found that the catalyst prepared from the complex could be stabilized only after a length of time. Therefore, preparation of the complex by using cyclohexane as the solvent should desirably be performed at a somewhat higher temperature than in the preparation using benzene as the solvent.

TABLE 3

|  | Days of catalyst storage | Catalytic activity, g α-olefin/ g ZrCl$_4$ | Composition of linear α-olefin product, % by weight | | | | | Purity of C$_{18}$ fraction, % by weight |
|---|---|---|---|---|---|---|---|---|
|  |  |  | C$_4$ fraction | C$_6$ fraction | C$_8$ fraction | C$_{10}$ to C$_{18}$ fraction | C$_{20}$+ fraction |  |
| Example 12 | 1 | 8020 | 14.9 | 15.0 | 14.1 | 40.2 | 15.8 | 95.4 |
|  | 5 | 8300 | 15.3 | 15.5 | 14.3 | 39.7 | 15.2 | 95.0 |
|  | 10 | 8050 | 15.1 | 15.4 | 13.9 | 40.1 | 15.5 | 95.4 |
| Example 13 | 1 | 6020 | 17.5 | 17.7 | 16.5 | 36.2 | 12.1 | 96.0 |
|  | 5 | 8100 | 14.8 | 15.1 | 14.1 | 39.9 | 16.1 | 95.3 |
|  | 10 | 8060 | 15.2 | 15.3 | 14.0 | 40.2 | 15.3 | 95.4 |

EXAMPLE 14

The experimental procedure was about the same as in Example 1 except that the solvent was cyclohexane instead of benzene, the amounts of zirconium tetrachloride, ethyl aluminum sesquichloride and triethyl aluminum were 0.05 m mole, 0.31 m mole and 0.09 m mole, respectively, to give the molar ratios of Al:Zr of 8 and (C$_2$H$_5$)$_3$Al$_2$Cl$_3$:(C$_2$H$_5$)$_3$Al of 3.5 and the complex solution was prepared at 70° C. taking 30 minutes. The results are shown in Table 4 below.

EXAMPLE 15

The experimental procedure was substantially the same as in Example 14 except that, in the preparation of the complex solution, zirconium tetrachloride was introduced following simultaneous introduction of triethyl aluminum and ethyl aluminum sesquichloride. The results are shown in Table 4.

EXAMPLE 16

The experimental procedure was substantially the same as in Example 14 except that, in the preparation of the complex solution, the three ingredients were successively introduced in an order of, first, triethyl aluminum, then, zirconium tetrachloride and, last, ethyl aluminum sesquichloride. The results are shown in Table 4.

COMPARATIVE EXAMPLE 7

The experimental procedure was substantially the same as in Example 14 except that, in the preparation of the complex solution, the three ingredients were introduced successively in an order of, first, ethyl aluminum sesquichloride, then, zirconium tetrachloride and, last, triethyl aluminum. The results are shown in Table 4.

EXAMPLE 17

The experimental procedure was substantially the same as in Example 14 except that, in the preparation of the complex solution, the three ingredients were introduced successively in an order of, first, triethyl aluminum, then ethyl aluminum sesquichloride and, last, zirconium tetrachloride. The results are shown in Table 4.

EXAMPLE 18

The experimental procedure was substantially the same as in Example 14 except that, in the preparation of the complex solution, the three ingredients were introduced successively in an order of, first, ethyl aluminum sesquichloride, then, triethyl aluminum and, last, zirconium tetrachloride. The results are shown in Table 4.

TABLE 4

| | Catalytic activity, g α-olefin/ g $ZrCl_4$ | Composition of linear α-olefin product, % by weight | | | | | Purity of $C_{18}$ fraction, % by weight |
|---|---|---|---|---|---|---|---|
| | | $C_4$ fraction | $C_6$ fraction | $C_8$ fraction | $C_{10}$ to $C_{18}$ fraction | $C_{20}+$ fraction | |
| Example 14 | 8400 | 16.2 | 16.3 | 14.6 | 40.5 | 12.4 | 95.0 |
| Example 15 | 8530 | 16.4 | 16.5 | 14.5 | 40.6 | 12.0 | 94.8 |
| Example 16 | 8380 | 16.6 | 16.6 | 14.8 | 40.2 | 11.8 | 95.1 |
| Comparative Example 7 | 2320 | 20.7 | 19.5 | 16.1 | 37.0 | 6.7 | 96.2 |
| Example 17 | 8380 | 16.7 | 16.6 | 14.8 | 40.2 | 11.7 | 95.0 |
| Example 18 | 8420 | 16.5 | 16.5 | 14.7 | 40.3 | 12.0 | 95.1 |

What is claimed is:

1. In a method for the production of α-olefin compounds by the oligomerization of ethylene in presence of a catalyst system which is a mixture composed
   (A) a zirconium halide compound represented by the general formula $$ZrX_aA_{4-a}$$

in which X and A, which may be the same or different from each other, are each an atom of a halogen selected from the group consisting of chlorine, bromine and iodine and the subscript a is zero or a positive integer not exceeding 4;
   (B-a) a first alkyl aluminum compound represented by the general formula $$AlR_{1.5}Q_{1.5}$$

in which R is an alkyl group having 1 to 20 carbon atoms and Q is an atom of a halogen selected from the group consisting of chlorine, bromine and iodine, R and Q each optionally being a combination of two kinds or more of the alkyl groups and halogen atoms, respectively; and
   (B-b) a second alkyl aluminum compound represented by the general formula $$AlR'_bQ'_{3-b}$$

in which R' is an alkyl group having 1 to 20 carbon atoms, Q' is an atom of a halogen selected from the group consisting of chlorine, bromine and iodine, R' and Q' each optionally being a combination of two kinds or more of the alkyl groups and halogen atoms, respectively, and b is 1, 2 or 3, and a ligand compound selected from the group consisting sulfur compounds, phosphorus compounds and nitrogen compounds improvement which comprises using a catalyst system compound of the components (A), (B-a) and (B-b) and prepared by a procedure in which:
   (1) the concentration of the zirconium halide compound as the component (A) is in the range from 40 to 140 m moles per liter of the solvent;
   (2) the temperature for the preparation of the catalyst system is in the range from 40° to 75° C. when the solvent is an aromatic hydrocarbon compound or in the range from 50° to 80° C. when the solvent is an alicyclic hydrocarbon compound;
   (3) the length of time for the preparation of the catalyst system is in the range from 30 minutes to 8 hours; and
   (4) the components (A), (B-a) and (B-b) are introduced in such an order that the second alkyl aluminum compound as the component is first introduced, then the zirconium halide compound as the component (A) is introduced and the first alkyl aluminum compound as the component (B-a) is lastly introduced.

2. The method of claim 1 wherein
   the zirconium halide, which is component A is ZrCl_4, ZrI_4, ZrBrCl_3 or ZrBr_2Cl_2;
   the first alkyl aluminum compound which is component (B-A), is
   $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3I_3$, $Al_2(C_2H_5)_3BrCl_2$, $Al_2(C_3H_7)_3Cl_3$, $Al_2(iso-C_3H_7)_3Cl_3$, $Al_2(C_4H_9)_3Cl_3$, $Al_2(iso-C_4H_9)_3Cl_3$, $Al_2(C_5H_{11})_3Cl_3$, $Al_2(C_8H_{17})_3Cl_3$, $Al_2(C_2H_5)_2(CH_3)Cl_3$
   the second alkyl aluminum compound, which is component (B-b), is
   $Al(CH_3)_3$, $Al(C_2H_5)_3$, $Al(C_3H_7)_3$, $Al(iso-C_3H_7)_3$, $Al(C_4H_9)_3$, $Al(iso-C_4H_9)_3$, $Al(C_5H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)Br_2$, $Al(C_2H_5)I_2$.

3. The method of claim 2 wherein the zirconium halide is $ZrCl_4$.

4. The method of claim 1 wherein
   $R_1$ is methyl, ethyl, propyl or butyl; and
   R' is ethyl, propyl or butyl.

5. The method of claim 4 wherein Q and Q' are chloro.

6. The method of claim 5 wherein $R_1$ and R' are ethyl.

7. The method of claim 6 wherein the zirconium halide is $ZrCl_4$, $ZrBr_4$, $ZrI_4$, $ZrBrCl_3$ or $ZrBr_2Cl_2$.

8. The method of claim 7 wherein the zirconium halide is $ZrCl_4$.

9. The method of claim 4 wherein the zirconium halide is $ZrCl_4$, $ZrBr_4$, $ZrI_4$, $ZrBrCl_3$ or $ZrBr_2Cl_2$.

10. The method of claim 9 wherein the zirconium halide is $ZrCl_4$.

11. The method of claim 1 wherein the zirconium halide is zirconium tetrachloride.

* * * * *

UNITED STATES PATENT AND TRADEMARK OFFICE
CERTIFICATE OF CORRECTION

PATENT NO. : 4,886,933

DATED : December 12, 1989

INVENTOR(S) : SHIRAKI et al

It is certified that error appears in the above-identified patent and that said Letters Patent is hereby corrected as shown below:

Column 13, line 39 (claim 1), after "production of",
    insert --linear-- .

Column 13, line 40 (claim 1), after "ethylene in",
    insert --the--.

Column 13, line 41 (claim 1), after "composed",
    insert --of:--.

Column 14, line 5 (claim 1), after "consisting",
    insert --of--.

Column 14, line 7 (claim 1), after "compounds",
    insert --, the --.

Column 14, lines 9-10 (claim 1), change "procedure" to
    --process--.

UNITED STATES PATENT AND TRADEMARK OFFICE
CERTIFICATE OF CORRECTION

PATENT NO. : 4,886,933

DATED : December 12, 1989

INVENTOR(S) : SHIRAKI et al

It is certified that error appears in the above-identified patent and that said Letters Patent is hereby corrected as shown below:

Column 14, line 24 (claim 1), after "component", insert --(B-b)--.

Column 14, line 46 (claim 2), after "$Cl_4$", insert --$ZrBr_4$,--.

Signed and Sealed this

Twelfth Day of January, 1993

Attest:

DOUGLAS B. COMER

Attesting Officer      Acting Commissioner of Patents and Trademarks